(12) United States Patent
Svetkoff et al.

(10) Patent No.: US 6,366,357 B1
(45) Date of Patent: *Apr. 2, 2002

(54) METHOD AND SYSTEM FOR HIGH SPEED MEASURING OF MICROSCOPIC TARGETS

(75) Inventors: Donald J. Svetkoff, Ann Arbor; Donald B. T. Kilgus, Brighton, both of MI (US); Warren Lin, Simi Valley, CA (US); Jonathan S. Ehrmann, Sudbury, MA (US)

(73) Assignee: General Scanning, Inc., Kanata (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/035,564

(22) Filed: Mar. 5, 1998

(51) Int. Cl.$^7$ .............................................. G01B 11/24
(52) U.S. Cl. ...................................... 356/602; 356/237.5
(58) Field of Search .............................. 356/376, 237.3, 356/375, 237.5, 394, 237.4, 237.1, 237.2, 601, 602, 611; 250/559.29, 559.22, 559.23, 559.31

(56) References Cited

U.S. PATENT DOCUMENTS

| | | |
|---|---|---|
| 3,013,467 A | 12/1961 | Minsky |
| 4,689,491 A | 8/1987 | Lindow et al. |

(List continued on next page.)

FOREIGN PATENT DOCUMENTS

| | | |
|---|---|---|
| RU | 868341 | 2/1982 |
| WO | WO 98/02716 | 1/1998 |

OTHER PUBLICATIONS

Brochure NM–2654A Panasert IP–K–V, "The Rotating Mirror Scan System Inspects Large High–Density PC Boards Quickly and Precisely", Specifications.

"Dynamic Focusing in the Confocal Scanning Microscope", T. Wilson and D.K. Hamilton, Journal of Microscopy, vol. 128, Pt. 2, Nov. 1992, pp. 139–143.

(List continued on next page.)

*Primary Examiner*—Hoa Q. Pham
(74) *Attorney, Agent, or Firm*—Brooks & Kushman P.C.

(57) ABSTRACT

A system including confocal and triangulation-based scanners or subsystems provides data which is both acquired and processed under the control of a control algorithm to obtain information such as dimensional information about microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The system includes a spatial filter for attenuating background energy. The triangulation-based subsystem also includes a detector of electromagnetic radiation which is placed at a second location which is non-collinear with respect to the incident beam. This detector has a position sensitive axis. Digital data is derived from signals produced by the detectors. In this way, data from at least one triangulation-based channel is acquired in parallel or sequentially with at least one slice of confocal image data having substantially perfect temporal and spatial registration with the triangulation-based sensor data. This allows for fusion or further processing of the data for use with a predetermined measurement algorithm to thereby obtain information about the targets.

16 Claims, 9 Drawing Sheets

U.S. PATENT DOCUMENTS

| | | | |
|---|---|---|---|
| 4,827,125 A | | 5/1989 | Goldstein |
| 4,863,226 A | | 9/1989 | Houpt et al. |
| 4,873,653 A | | 10/1989 | Grosskopf |
| 4,893,008 A | | 1/1990 | Horikawa |
| 5,024,529 A | | 6/1991 | Svetkoff et al. |
| 5,118,192 A | | 6/1992 | Chen et al. |
| 5,153,428 A | | 10/1992 | Ellis |
| 5,239,178 A | | 8/1993 | Derndinger et al. |
| 5,248,876 A | | 9/1993 | Kerstens et al. |
| 5,381,236 A | | 1/1995 | Morgan |
| 5,448,359 A | | 9/1995 | Schick et al. |
| 5,479,252 A | | 12/1995 | Worster et al. |
| 5,483,055 A | | 1/1996 | Etzbach et al. |
| 5,510,894 A | | 4/1996 | Batchelder et al. |
| 5,546,189 A | | 8/1996 | Svetkoff et al. |
| 5,594,235 A | | 1/1997 | Lee |
| 5,617,209 A | | 4/1997 | Svetkoff et al. |
| 5,654,800 A | * | 8/1997 | Svetkoff et al. ............ 356/376 |
| 6,098,031 A | * | 8/2000 | Svetkoff et al. ............ 702/159 |

OTHER PUBLICATIONS

"Digital Image Processing of Confocal Images", I. J. Cox and C.J.R. Sheppard, Image and Vision Computing, vo. 1, No. 1, Feb. 1983, pp. 52–56.

"Three–Dimensional Surface Measurement Using the Confocal Scanning Microscope", D.K. Hamilton and T. Wilson, Appl. Phys. B 27.211–213 (1982).

"Scanning Optical Microscope Incorporating a Digital Framestore and Microcomputer", I.J. Cox and C.R. Sheppard. Applied Optics, vol. 22, No. 10, May 15, 1983, pp. 1474–1478.

"Depth of Field in the Scanning Microscope", C.J.R. Sheppard and T. Wilson, Optics Letters, Sep. 1978. vol. 3, No. 3, pp. 115–117.

"NLB Laser Inspector, NLB–7700M Specifications", Nagoya Electric Works Co., Ltd. Dec. 1994.

"Automatic Inspection of Component Boards Using 3D and Greyscale Vision", Donald J. Svetkoff, David N. Smith and Brian L. Doss, Proceedings of the 1986 International Symposium on Microelectronics, pp. 57–64.

\* cited by examiner

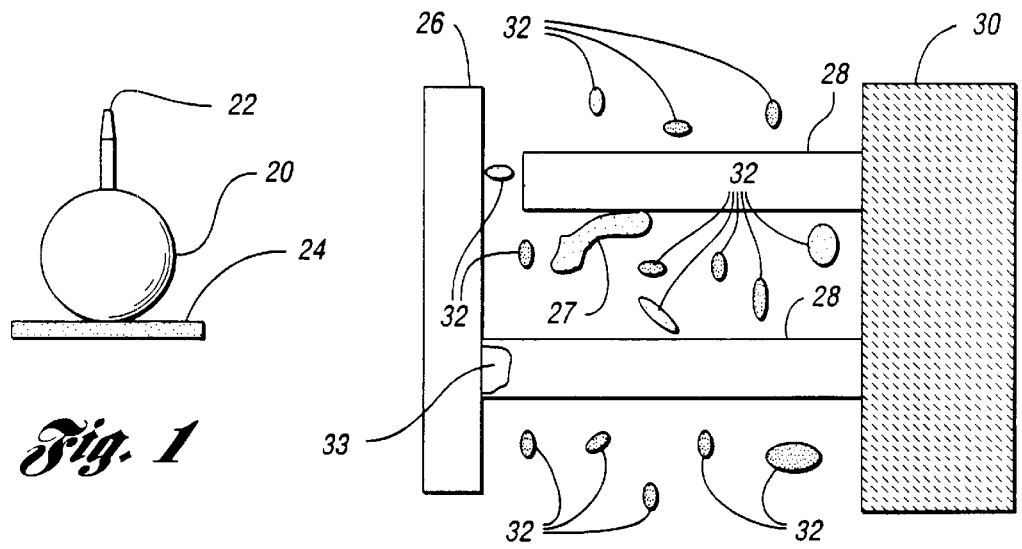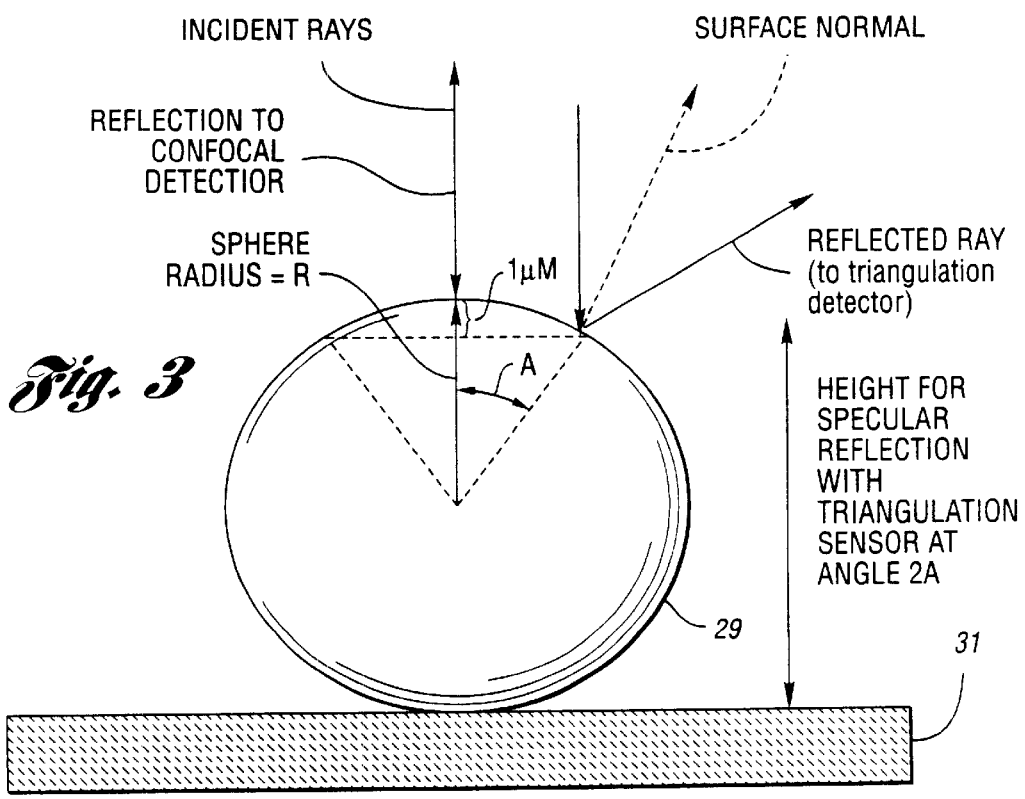

METHOD AND SYSTEM FOR HIGH SPEED MEASURING OF MICROSCOPIC TARGETS

CROSS-REFERENCE TO RELATED APPLICATION

This application is related to U.S. patent application ///Ser. No. entitled "Versatile Method and System for High Speed, 3D Imaging of Microscopic Targets" filed on the same day as this application.

TECHNICAL FIELD

This invention relates to methods and systems for high speed measuring of targets and, in particular, to methods and systems for high speed measuring of microscopic targets which may be "non-cooperative."

BACKGROUND ART

Recognition of Need

A class of three-dimensional imaging and measurement applications now requires unprecedented demonstration of capability to support new microelectronic and micromechanical fabrication technologies. For example, emerging semiconductor fabrication technologies are directed toward establishing a high density of interconnection between the chip and package. The "bumped wafer" and miniature ball grid array ("$\mu$-BGA") markets are emerging, and large scale growth is predicted. For instance, NEMI (National Electronics Manufacturing Initiative) has clearly indicated that the miniature array technologies are to replace traditional wire bonding interconnects. Manufacturers are experimenting with new processes. Measurement tools to support their efforts will require versatility.

For example, "dummy wafers" are used for many experiments, which have a specular and featureless surface onto which interconnects are placed. The appearance is much different than patterned wafers seen in typical production environments. This imaging phenomena is of little concern to the process engineer. In fact, the most difficult imaging problems may coincide with the best choice of process. Industry process development engineers indicate that reflowed spherical solder bumps with a smooth surface finish, sometimes a nearly perfect mirror, may be the preferred technology for the chip interconnects. The surface reflectance will vary because of process engineers' choices of relative content of lead and tin. Such targets are often "uncooperative."

The chips onto which the balls are placed are subsequently attached to printed circuit boards where both flattened and spherical mating interconnects can be expected, with either a dull or smooth surface finish. All combinations are expected. Other geometric shapes (wire with flat top, cones) can be expected in the future which will pose measurement challenges, particularly when the surface is specular with spherical or cylindrical geometry, including concavities.

Such "non-cooperative" targets, ( i.e. those which present challenges for measurement systems as a result of light reflection, scattering, and geometry), are and will continue to be growing in occurrence for semmiconductor micromachining, and mass storage imaging applications. A specific growing need is recognized for an imaging system capable of improving dimensional measurement of $\mu$-BGAs and bumped wafers (i.e. "spherical mirrors" on variable wafer backgrounds) and other such targets, which are "non-cooperative" with respect to traditional imaging systems. As inspection and measurement requirements for industries requiring microscopic measurement capabilities, for instance semiconductor and mass storage, become more demanding, extraordinary versatility will be needed for handling wide variation in scale, target geometry, and reflectivity. Similarly, inspection and measurement of circuit boards and the dielectric and conductive materials requires a versatile imaging system, particularly for fine geometries and densely populated component boards.

As mentioned previously, imaging requirements for the semiconductor packaging industry include defect detection as part of Package Visual Inspection (PVI), measurement of $\mu$-BGA height, coplanarity, diameter, and wafer defects. High resolution and image clarity obtained from reduction of image artifacts are both required for adequate process characterization. Problems similar to those in the semiconductor area are also present when measuring other miniature parts like micromachined (micromechanical) assemblies, like miniature gears and machines, and components utilized in the mass storage industry, including substrates, disk heads, and flexures.

For example, as illustrated in FIGS. 1 and 7, inspection of a very fine solder bump or ball 20 with a "pin" or tip 22 necking down to about 1–$\mu$m in dimension mounted on a solder pad 24, poses a measurement problem. Manufacturers often examine the tip 22 with an electron microscope for initial evaluation, but such a tool is much too slow for detailed process characterization or real time control.

Also, detection of small "hairline" burrs on IC leads is often successful using gray or 3D data using only triangulation, but false alarms are common because background noise and reflection from a container, such as a tray wall 26, can appear similar to the defect such as a burr 27, as illustrated in FIG. 2. Conversely, IC leads 28 of an IC chip 30 may be indistinguishable from the background noise 32. These false alarms are unacceptable and lower yields, thereby decreasing the value of inspection equipment.

$\mu$-BGA inspection can be roughly equivalent to measuring a tiny "spherical mirror" (solder ball) mounted on a plane "mirror" (wafer) background; yet, in other cases, where the wafer is patterned and the ball has a lower tin content, is a completely different imaging problem. Solutions to such measurement problems will require versatility for handling the geometric shape and reflectance variation.

Hence, with wafer scale and other sub-micron measurement tasks, the challenges with material properties will grow, not diminish. There is a need to measure substrates, conductors, and thickness of films, or the geometry of micromechanical assemblies such as miniature gears having deep, narrow dimensions and varying optical properties, including partially transparent layers.

Prior Art Technology

Early work on defect detection of features having specular components using camera-based inspection is described in U.S. Pat. No. 5,058,178 and the references cited therein. The method is primarily directed toward lighting and image processing methods for defect detection of bumped wafers. The lighting system included combinations of bright and dark field illumination. Measurement of the diameter can be done with a camera system and appropriate illumination, but accuracy is often limited by light scattering and limited depth of focus when high magnification is required. However, in addition to defect detection and bump presence, there is a need to measure the three dimensional geometry of the bumps for process characterization. The bumps must be coplanar to provide a proper connection, and the diameter within tolerance for a good connection with the bonding pads.

Triangulation is the most commonly used 3D imaging method and offers a good figure of merit for resolution and speed. U.S. Pat. Nos. 5,024,529 and 5,546,189 describe the use of triangulation-based systems for inspection of many industrial parts, including shiny surfaces like pins of a grid array. U.S. Pat. No. 5,617,209 shows an efficient scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability as disclosed in the publication entitled "Automatic Inspection of Component Boards Using 3D and Grey Scale Vision" by D. Svetkoff et al., PROCEEDINGS INTERNATIONAL SYMPOSIUM ON MICROELECTRONICS, 1986.

Confocal imaging, as originally disclosed by Minsky in U.S. Pat. No. 3,013,467, and publications: (1) "Dynamic Focusing in the Confocal Scanning Microscope" by T. Wilson et al.; (2) "Digital Image Processing of Confocal Images" by I. J. Cox and C. J. R. Sheppard; (3) "Three-Dimensional Surface Measurement Using the Confocal Sensing Microscope" by D. K. Hamilton and T. Wilson; (4) "Scanning Optical Microscope Incorporating a Digital Framestore and Microcomputer" by I. J. Cox and C. J. R. Sheppard; and (5) "Depth of Field in the Scanning Microscope" by C. J. R. Sheppard and T. Wilson, is similar to computerized tomography where slices in depth are sequentially acquired and the data is used to "reconstruct" a light scattering volume. In principle, an image is always formed of an object at a focal plane as taught in elementary physics, but over a region of depth there are an infinite number of planes which are out of focus yet return energy. That is to say that the lens equation for image formation is based on an idealization of an "object plane" and "image plane".

In the case of conventional confocal imaging, the slices are determined from the in-focus plane, and out-of-focus light (in front and back of the focal plane) is strongly attenuated with a pinhole or slit. Typical confocal systems use fine increments for axial positioning for best discrimination between adjacent layers in depth, for example, semi-transparent biological samples. However, the method need not be restricted to the traditional transparent or translucent objects, but can be applied both as a depth measurement tool and image enhancement method using reflected light for contrast improvement through stray light rejection. As with any method, there are advantages and disadvantages.

Application of confocal imaging to semiconductor measurement is disclosed in U.S. Pat. Nos. 4,689,491, 5,479,252 and 5,248,876. Operation of several confocal systems is described in U.S. Pat. Nos. 4,827,125; 4,863,226; 4,893,008; 5,153,428; 5,381,236; 5,510,894; 5,594,235; and 5,483,055 and H 1,530. Much of the recent work is directed toward improvements, resulting in reduction of the image memory storage requirements (store maximum, not volume), improving the efficiency and fine positioning capability of autofocus systems (coarse/fine search), exposure control for improved dynamic range, and some image enhancement methods.

Similarly, variations in confocal acquisition methods are taught in the art to solve specific problems or optimize designs for specific applications as taught in U.S. Pat. Nos. 5,239,178 and 4,873,653. However, present confocal systems are constrained by sequential slicing of the volume, whereas triangulation systems detect the top surface of the volume (profile) directly resulting in much higher speed.

In U.S. Pat. No. 5,448,359 such speed limitations are partially circumvented by utilizing a plurality of detectors and spatial filters in the confocal receiver optical path. A circuit to locate the detector producing maximum intensity is disclosed.

Similarly, USSR patent document No. 868,341 discloses a plurality of detectors with apertures (confocal) and electronic circuitry to obtain focus (3D) information about objects. The intensity of each detector is compared and used to adjust the position of the imaging system along the optical axis so as to clear the mismatch. In each case, a tradeoff is determined between depth sensitivity, complexity, and measurement speed.

Other approaches to imaging of "non-cooperative" targets, many directed toward solder joint inspection, have been proposed to measure depth or fillet shape. These are described in the U.S. patent to Chen et al. 5,118,192 and a Nagoya solder joint inspection system described in "NLB Laser Inspector—NLB-7700M Specifications" by Nagoya Electric Works Co., Ltd. 1994. The system uses specularly reflected light to examine the shape of solder fillets, and to determine presence/absence of solder. Figure E in Section 6 thereof shows a missing fillet and the signals received from a plurality of detectors. A detector 6 corresponds to an "on-axis" detector, and the information is useful for estimating the diameter of the solder bump. For instance, the detector 6 receives a large signal near the top of the ball, a weak signal from the curved edge, and typically a strong signal from the area adjacent to the bump. However, narrow angle multiple reflections from the edge of the ball can corrupt the measurement and result in ambiguous edge locations. Furthermore, the sensitivity of the system may not be adequate to determine the height of regions which do not have a substantial specular reflection component.

Similarly, a recent version of the IPK solder joint inspection system manufactured by Panasert includes a coaxial detector with a triangulation-based sensing system as illustrated in their brochure entitled "IPK-V" believed to be published in 1997. The $\mu$-BGA, bumped die, and numerous other problems range from scenarios where prior art technology is adequate, but in many cases unacceptable, and even inoperable conditions exist.

Wafer measurement and defect detection systems have utilized multiple detectors advantageously. U.S. Pat. No. 5,416,594 describes a system which uses both reflected and scattered light for detection of defects and thin film measurements. The reflected beam is received at an angle of reflection which is non-collinear with the transmitted beam and the scattered light is collected over a relatively large angle which excludes the reflected beam energy. The scattered light beam, representative of surface defects, may be collected at an angle which is widely separated (more than 30 deg.) from the incident beam. The off-axis illumination and the corresponding reflected beam are utilized for film thickness measurements, sometimes with multiple laser wavelengths. The scattered light signal is analyzed in conjunction with that representing the reflected light. Although the imaging geometry is well matched to the specific cited inspection requirements, there are several potential disadvantages encountered when attempting to simultaneously provide information about surface defects and say, the peak height of interconnects like solder bumps (which have substantial height) and the corresponding diameter and shape.

Commercial success has not been widespread, although many approaches have been proposed. Hence, there is a need for a system and method for three-dimensional imaging capable of performing with both "cooperative" and "non-cooperative" targets. To be useful, the method and system must be accurate, robust, and have high measurement speed, the latter being a traditional limit to the use of widespread confocal imaging.

SUMMARY OF THE INVENTION

A method of the present invention overcomes the limitations of the prior art imaging of non-cooperative targets by illuminating a surface with a scanning beam, acquiring data from at least one triangulation-based channel, and acquiring in parallel or sequentially at least one slice of confocal image data having substantially perfect temporal and spatial registration with the triangulation-based sensor data, allowing for fusion or processing of the data for use with a predetermined measurement algorithm.

The objects of a system of the present invention are met by utilizing a combination of confocal and triangulation-based data acquisition, with a control algorithm guiding the cooperative data acquisition and subsequent processing.

The invention is a method and system for developing three-dimensional information about an object by illuminating an object with a focused beam of electromagnetic radiation incident from a first direction. A detector of electromagnetic radiation is placed at a first location for receiving reflected radiation which is substantially optically collinear with the incident beam of electromagnetic radiation, and the detection system includes a spatial filter for attenuating background energy. Another detector of electromagnetic radiation is placed at a second location which is non-collinear with respect to the incident beam. The detector has a position sensitive axis. Digital data is derived from signals produced by said first and second detectors. The digital data is then processed to generate information about the object.

Specific objects of the invention include:

An object of the invention is to provide an integrated method and system for high speed measuring to obtain measurements for conductor traces (height ~1–3 $\mu$m) and/or interconnects (i.e. 10–300 $\mu$m bumps) on semiconductor devices.

An object of the invention is to provide a method and system for high speed measuring which has diverse measurement and defect detection capability with a combination of a confocal sensor and triangulation allowing for measurement of miniature, complex geometry present in the microelectronics, micromechanical, and disk storage industries.

An object of the invention is to provide a method and system for high speed measuring to obtain information from either of two channels used to guide subsequent data acquisition operations in either or both channels. For example, sparse data may be acquired with a triangulation-based system at high speed, and the information used to guide the high speed selection of confocal slices, perhaps in windowed regions. FIG. 3 illustrates imaging geometry of a solder ball 29 (i.e. spherical mirror) of radius R (i.e. R<150 $\mu$m typically) formed on a pad 31.

An object of the invention is to provide a high speed method and system for measuring which can obtain reasonable height estimates of the bumps or "spherical mirrors" in a "pre-screening" operation and locate defective bumps or wafers at high speed. The results would define the range for additional slices (i.e. if needed) for precise verification of the geometry of regions passing the "pre-screening" test. Therefore, maintaining wafer inspection times will remain as minutes, not hours. For "sparse" patterns, "windowing" could increase the speed of measurement for localized regions. FIGS. 4a and 4b are top schematic images of specular solder balls 34 (indicated by phantom lines in FIG. 4a) using triangulation and confocal imaging, respectively, in accordance with the present invention. The balls 34 of FIG. 4b have specular ball tips 35 formed on pads 36 which, in turn, are located on a shiny "dummy" wafer 38. The 3D image of FIG. 4a (i.e. including specular reflections from regions 35' of the ball 34 adjacent the ball tips) is formed by a triangulation-based system having dual detectors to provide Z measurement, bump presence and defect information. The confocal slice image of FIG. 4b provides diameter, Z measurement and defect information. In both FIGS. 4a and 4b, a flat bump having diffuse reflection is indicated at 40, an empty pad (i.e. missing bump) is indicated at 42, and a smashed bump (i.e. defect) is indicated at 44.

Referring specifically to FIG. 5, an object of the invention is to provide a high speed method and system for measuring a miniature spherical mirror like a solder ball 46 or wafer, mounted on a plane mirror or pad 48 formed on a substrate 50 and producing a very high contrast bump-background image allowing for accurate measurement of diameter, devoid of occlusion and with minimal reflection noise for many pad backgrounds. FIG. 5 shows a spatial filter 52 through which an incident ray 54 passes and bounces off the ball surface to form reflected rays 56, multiple reflections 58, and specular reflection 60. The spatial filter 52 (i.e. confocal slit) provides the indicated filtering action.

An object of the invention is to provide a high speed method and system for measuring which have significant advantages over conventional camera and lighting systems, even with relatively few slices of spatially filtered data.

An object of the invention is to provide a high speed method and system for measuring to, in turn, provide gray scale contrast improvement of the image of FIG. 2 for possible detection of defects and reduction of false "accepts" and "rejects" (i.e. "error" region 33) in any number of applications through stray light rejection. One such classification of burrs 27 and similar defects, like those specified for electronic Package Visual Inspection (PVI), may be satisfied with this method and system and would otherwise be difficult. FIG. 6 is a confocal slice of the IC chip 30 of FIG. 2 located in the tray 26 of FIG. 2. FIG. 6 illustrates the effect of spatial filtering with best focus near the nominal pad and burr locations. With the present invention, the data of FIG. 6 is combined with 3D triangulation data for improved classification. Also, visualization and measurement of small bumps and pits could be improved. Furthermore, discrimination of edges which is difficult in the presence of multiple reflection is provided herein.

An object of the invention is to provide a high speed method and system for measuring to, in turn, overcome limits of triangulation-based imaging for "mirrored" wafer backgrounds, where triangulation often requires photon limited detection or nearly so, and to provide a focus-based depth measurement method and system which operates at high speed.

An object of the invention is to provide a method and system for measuring at high speed for measurement of ball bumps, and rigid wire interconnects within the semiconductor industry.

Referring again to FIGS. 1 and 7, an object of the invention is to provide a method and system for high speed measuring of objects having complex geometry, for instance "ball bumps" 20 and rigid wires 22, with the speed advantages of a triangulation/confocal combination while overcoming "enclosed energy" limitations and resulting corruption of the "signal" by optical noise from reflection of the sidelobe energy to the background (as illustrated in FIG. 7), producing false readings in triangulation-based systems. In this case, a confocal channel produces a higher optical signal-to-noise and background rejection, while a triangulation-based system rapidly measures the other features, albeit at least two passes might be required because of the pin height relative to the necessarily restricted depth of focus.

An object of the invention is to provide an integrated method and system for high speed measuring having substantially perfect temporal and spatial registration between two sensors or subsystems of the system which allows "fusion" of the data, with selection of the best sensor data based upon reflectance and contrast, perhaps on a pixel-by-pixel basis.

An object of the invention is to provide a versatile method and system for high speed measuring of targets on the wafer scale for inspection and measurement. At such higher magnification, material properties vary greatly, from translucent to opaque, and "mirror-like" to matte.

An object of the invention is to provide a method and system for high speed measuring to provide improved discrimination of metallic surfaces from the translucent backgrounds, and to measure materials such as conductive epoxy used for interconnects. Some applications in the optical storage industry may be best solved with this type of technology (flexure measurement) and at higher magnification (high contrast, disk head measurement).

An object of the invention is to provide a method and system for high speed measuring which introduces a feature of increased gray scale contrast and fidelity from the region of the beam waist, through at least rudimentary "depth-through-focus detection" capability. At very high magnification, a confocal channel either "competes" or "cooperates" with dual-detector triangulation for the best imaging mode.

An object of the invention is to provide an integrated method and system for high speed measuring which can include both high N.A. (numerical aperture) optics and lower N.A. for use with either confocal or triangulation channels realized with wavelength, time or spatial multiplexing methods, as illustrated in FIG. 8.

An object of the invention is to provide a method and system for high speed measuring which provides selectable lateral and depth resolution for confocal and triangulation-based imaging through the use of multiplexing and programmable or selectable height resolution.

An object of the invention is to provide a method and system for high speed measuring including high grey scale resolution and dynamic range (sufficient to avoid automatic gain or light control requirements) and processing with smoothing algorithms. The smoothing algorithms may be adapted to include known information regarding the physical characteristics of the object.

An object of the present invention is to provide a method and system for high speed measuring by obtaining confocal and/or triangulation data rapidly. Objects which are reflective, such as solder joints, substrates and wafers are substantially opaque in a homogeneous medium such as air, unlike several objects traditionally "sliced" with the confocal technique. As such, an object of the invention is to estimate the depth of reflective objects using estimation techniques and relatively few slices compared to traditional "peak detection" systems utilized for confocal imaging. The smoothing and estimation techniques could be utilized with a single confocal detector when data is acquired with axial translation, with multiple detectors involving no translation or a combination of the two.

A further object of the present invention is to provide a method and system for high speed measuring by adapting smoothing and/or estimation algorithms based upon a priori information regarding the physical characteristics of objects within a region of interest, thereby avoiding corruption of the measurements associated with peak search methods.

A further object of the invention is to provide measurement capability of both "featureless" and textured surfaces using an appropriate selection of information.

An object of the invention is to provide an improved method of measuring using confocal imaging, used alone or in combination with triangulation, where acquisition times are reduced with the use of a solid state beam deflector having retrace times on the order of 1–10 microseconds, whereby pixel rates well in excess of video rates are achievable.

A further object of the invention is to provide an improved method of measuring using confocal imaging where mechanical motion requirements for axial translation of the position of focus of the illumination beam is reduced or eliminated.

In carrying out the above objects and other objects of the present invention, a method is provided for developing dimensional information about an object on a specular background utilizing a scanning system having a sensor. The scanning system scans an illumination beam of electromagnetic energy. The method includes the step of determining reference data based on an illumination beam reflected from the specular background. The method further includes the step of positioning the sensor based on the reference data so that a waist of the illumination beam substantially coincides with an expected predetermined 3D location of the object so as to enhance contrast and obtain three-dimensional sensor data and/or confocal sensor data. The method finally includes the step of processing the sensor data to obtain the dimensional information.

Still further in carrying out the above objects and other objects of the present invention, a system is provided for developing dimensional information about an object. The confocal system includes at least one illuminator for illuminating the object with at least one beam of electromagnetic energy to obtain at least one reflected beam of electromagnetic energy, a confocal detector for detecting the at least one reflected beam of electromagnetic energy and producing at least one signal, a signal processor for processing the at least one signal to obtain confocal data and a data processor having digital data processing data smoothing and curve fitting algorithms for processing the confocal data with a priori knowledge about the object to obtain the dimensional information whereby the accuracy of the confocal data is improved (i.e., particularly with the use of fewer slices acquired at relatively coarse increments with respect to the attainable height resolution).

Further in carrying out the above objects and other objects of the present invention, a method is provided for inspecting bumps on a wafer. The method includes the steps of acquiring reference data based on 3D information obtained from either a confocal subsystem or a triangulation subsystem having a triangulation sensor. The method further includes the step of generating a scan based upon the reference data to obtain 3D data wherein the 3D data is obtained from the triangulation sensor. The method finally includes the step of determining height of the bumps based on the 3D data.

Yet still further in carrying out the above objects and other objects of the present invention, a method is provided for developing dimensional information about an array of objects, each of the objects including a surface. The method includes the steps of obtaining a first set of data representing maximum specular reflections from the surfaces of the objects, computing height estimate data for the array of objects utilizing the first set of data and analyzing the height estimate data to obtain an estimate of the height.

In further carrying out the above objects and other objects of the present invention, a method is provided for measuring at least one dimension of an interconnect on a specular wafer. The method includes the step of measuring the wafer at three or more non-colinear locations to obtain reference data. The method includes further includes forming a reference plane from the reference data. The method also includes the step of scanning the wafer to obtain scan data based on the reference plane. The method finally includes the step of determining the at least one dimension of the interconnect based on the scan data.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 is a schematic side view of a ball bump with an interconnecting wire;

FIG. 2 is a top schematic view of a 3D image of leads and defects in a tray using only triangulation and illustrating an error caused by tray wall reflection;

FIG. 3 is a side schematic view of a specular solder ball on a wafer and illustrating the ball's imaging geometry;

DESCRIPTION OF THE PREFERRED EMBODIMENT

Figure 9:
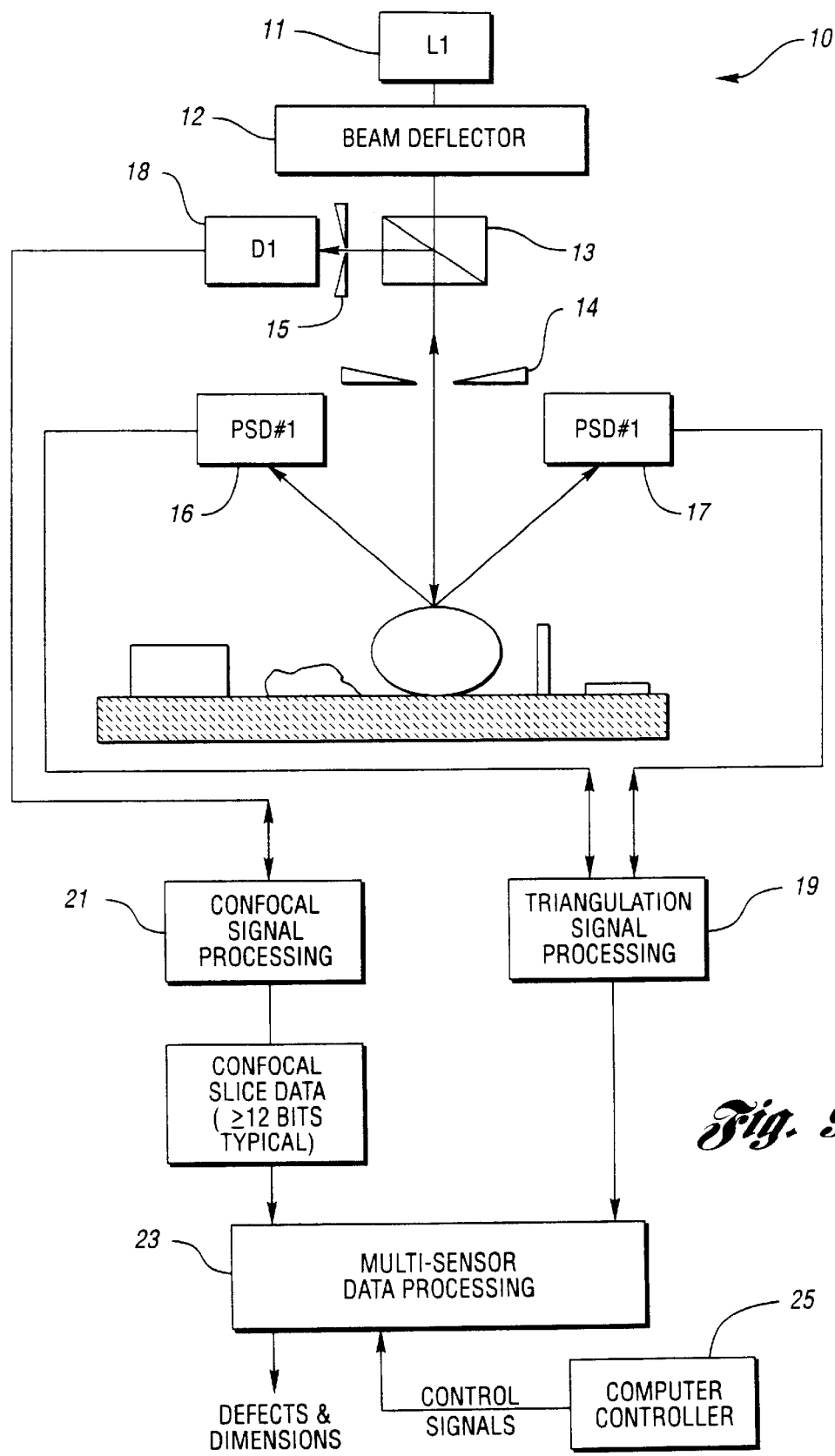
FIG. 9 is a schematic view of a simplified combined triangulation and confocal system constructed in accordance with the present invention without optical elements.

FIG. 9 is a simplified schematic view, without optical elements, of an integrated triangulation-confocal system, generally indicated at 10, constructed in accordance with the present invention. The system 10 includes a laser 11 (i.e. L1), a beam deflector 12 and a beam splitter assembly 13. The system 10 also includes a pair of spatial filters in the form of slits 14 and 15. The system 10 further includes first and second position sensitive detectors 16 and 17, respectively, and a photodiode detector 18. The detectors 16 and 17 provide triangulation analog signals to a triangulation signal processor 19 for triangulation signal processing and the detector 18 provides confocal analog signals to a confocal signal processor 21 for confocal signal processing. The resulting digital Z (i.e. height) and grey scale data from the processor 19 is combined with digital confocal slice data ($\geq$12 bits typical) from the processor 21 by a data processor 23 which provides multi-sensor data processing under the control of a computer controller 25 to obtain defect and dimensional data for the object being inspected by the system 10.

Figure 10:
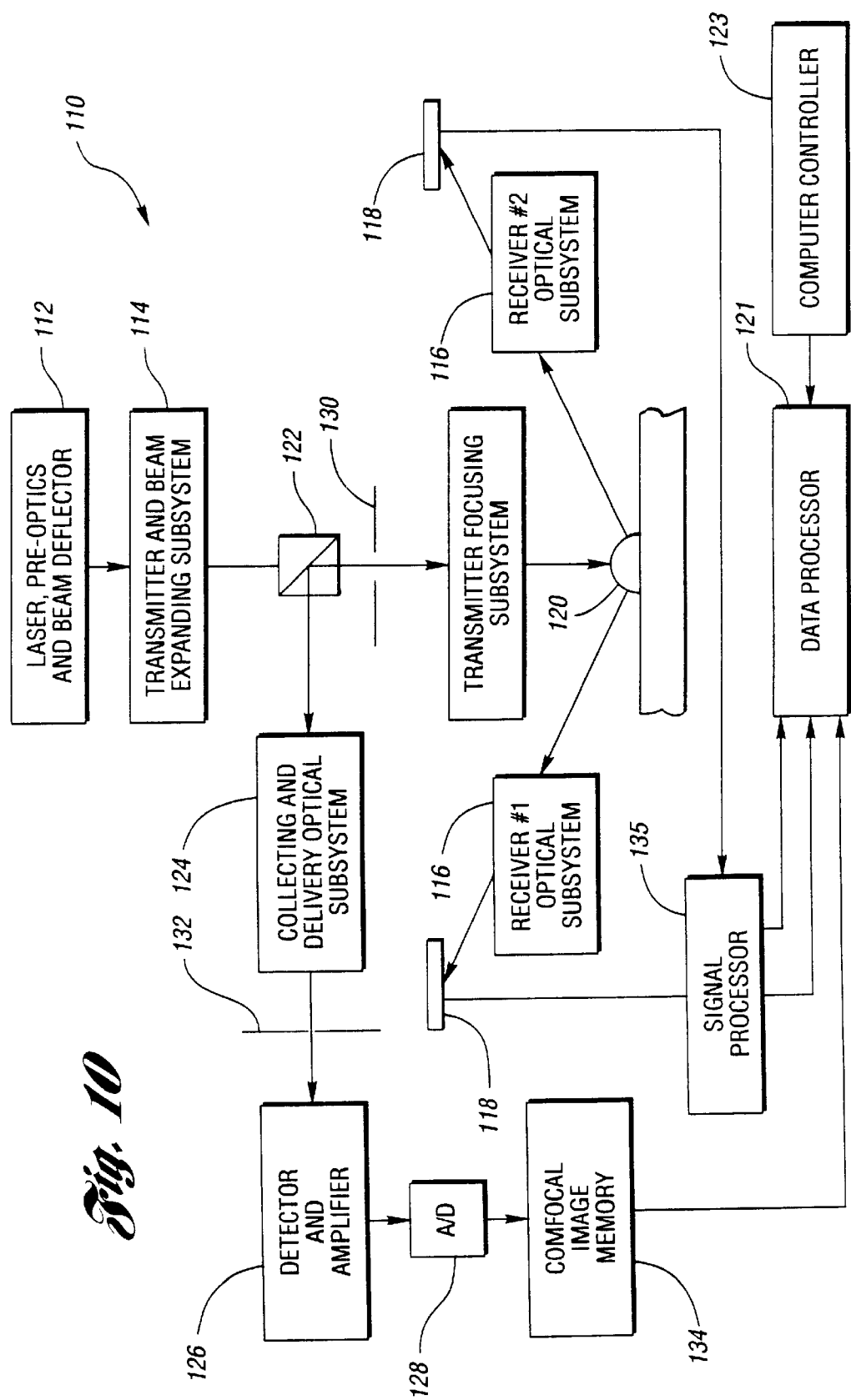
FIG. 10 is a schematic view of a combined triangulation and confocal system constructed in accordance with the present invention.

FIG. 10 shows a schematic representation, together with optical elements, of an integrated triangulation-confocal system, generally indicated at 110, constructed in accordance with the present invention. The system 110 generally includes a triangulation-based laser scanner 112. The triangulation-based laser scanner 112 has optical elements (i.e. pre-optics), a beam deflector, and a laser transmitter. The operation of triangulation-based laser scanners is taught in the art. For example, U.S. Pat. No. 5,024,529 shows a preferred method for high speed, triangulation-based imaging.

The system 110 also includes a transmitter beam expansion subsystem 114 and a transmitter focusing subsystem 115. The system 110 further includes a pair of receivers, each of which includes an optical subsystem 116 and a position sensitive detector 118 which are positioned at angles with respect to a laser beam incident on an object 120 which may have a spherical surface. Each optical subsystem 116 preferably includes an anamorphic optical assembly to delivery energy to its small area detector 118 whereby speed, field of view, and signal-to-noise ratio are maximized.

Figure 11:
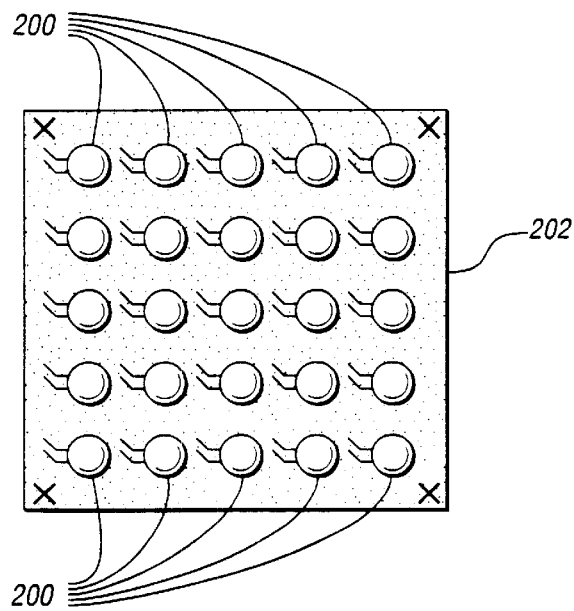
FIG. 11 is a top schematic view of a semiconductor die enlarged from FIG. 12 with spherical mirror balls mounted thereon.
Figure 12:
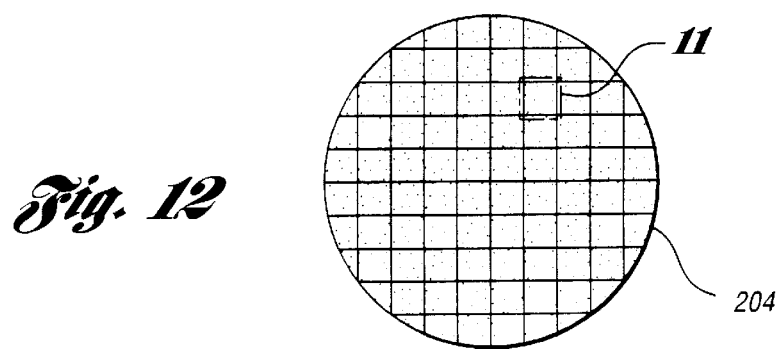
FIG. 12 is a top schematic view of a wafer having a plurality of dies to be inspected.

The multiple detectors 118 are preferably used to improve the accuracy of triangulation-based measurements by transforming height and intensity data based on confidence measures as taught in U.S. Pat. No. 5,546,189. Based upon specifications for inspection and knowledge of the object structure, either data channel can be used, or a knowledge-based algorithm can be used on a data processor 121 under control of a computer controller 123 to merge the resulting z and grey scale level data. Efficient scanning methods to exploit regular or repetitive patterns such as balls or bumps 200 formed on a die 202 as illustrated in FIG. 11 are known and taught in the art. For example, the symmetry of row/column arrangements can be exploited as taught in U.S. Pat. No. 5,617,209. Such regular arrangements are found in the semiconductor industry and others. Each ball 200 is typically 10–300 μm in diameter. The die 200 is an enlarged part of a wafer 204 shown in FIG. 12. The wafer 204 is typically 6 inches in diameter.

Referring again to FIG. 10, a basic confocal subsystem is integrated with the above-described triangulation-based scanning subsystem to offer combined triangulation and confocal capability. A confocal channel is added with the addition of a beam splitter assembly 122, a collection and delivery optical subsystem 124, a photodiode detector/amplifier 126, and preferably an "on-board" high resolution analog-to-digital converter 128 (i.e., 12–16 bits).

A spatial filter having a relatively wide slit 130 reduces laser and optical system spatial noise and provides the dual function of a confocal slit to filter back-scattered light displaced from the plane of best focus and secondary reflections from outside the narrow instantaneous field of view. Preferably, a second spatial filter having a relatively narrow slit 132 is located between the subsystem 124 and the detector/amplifier 126. This allows for improvements or adjustments in sensitivity without the risk of introducing diffraction effects into the transmitted beam (i.e. the incident beam). The separate path is optionally provided by the narrow slit 132 if increased sensitivity is required. In addition, the use of additional slits and detectors (or multiple laser beams) provides an option for variable sensitivity to reduce possible tradeoffs in measurement time.

From a practical standpoint, it is desirable that the dimensions of the slits 14 (i.e. FIG. 9) and 130 be about 3–5 times a diffraction-limited spot diameter. Finer discrimination is possible with the addition of a tracking mechanism, perhaps with use of a piezoelectric controller to compensate for any drift with time or temperature. The use of a single slit is an option, but is not an essential element of the invention.

A narrow slit width is not always a crucial feature of the invention because a defocus function can often be sampled at coarser intervals of depth and interpolation or curve fitting methods used to estimate the height at the point of interest. If spatial filtering of the incident beam is not warranted and hence is not implemented, a single confocal slit 15 and 132 may be used in the separate beam path. In any case, if a very narrow slit is used, active stabilization may be needed to avoid an increase in intensity noise induced by drift, microphonics, or other external influences. The above embodiment allows for high definition confocal imaging without disturbing the triangulation image with undesirable diffraction effects.

The assembly 122 preferably includes a cube beam splitter which serves the dual purpose of providing optical isolation to prevent feedback light from entering the laser cavity, and a relay system to deliver light to the high speed detector 126. The best delivery system will be designed to uniformly fill the detector 126 so as to avoid errors associated with intensity variations along the detector surface.

Neutral density filters or LCDs can be used for static or dynamic exposure control. If an acousto-optic beam deflector is used, optical attenuation can be controlled with RF drive power. Fast modulation methods may also be implemented with either acousto-optic modulators or electro-optic modulators. The latter is preferably implemented in a waveguide structure for maximum speed, compactness, and minimal power dissipation. However, advancements in A–D converter technology have resulted in 14–16 bit converters which operate at video speeds or greater. These devices, along with advancements in memory speed and density, may often eliminate the requirement of exposure control. Such technology, along with wide dynamic range detectors, is preferred. However, the directional reflectance of many industrial objects spans about 4 decades, so exposure control may be required in some cases for sufficient noise margin.

Subsequent to A–D conversion by the converter 128, an interface is needed to acquire the multiple channels of data. For instance, a confocal PCI-based image acquisition scan buffer or commercially available frame grabber or a confocal image memory 134 is provided. The memory 134 is connected to the data processor 121 for processing its output with the Z and grey outputs of a signal processor 135 which processes the output of the detectors 118 as described below.

Continued advancements in high speed digital data transmission methods can be used to minimize the number of components. For example, commercially available A–D boards providing 12 bits at 30 MHz data rates are available presently, like the Compuscope Series from Gage Applied Sciences. Such advancements are advantageous because the triangulation (with single or dual detectors) data and the confocal image can be readily acquired and stored in parallel, resulting in perfect temporal and spatial registration for "fusion" operations in the processor 121. Other alternative methods are known to those skilled in the art including "fire-wire" technology for digital transmission to PC memory.

In any case, it is clear that future revisions of hardware will not be a stumbling block because memory is cheaper and will require less space, and processors will be able to handle multiple imaging modes. Indeed, it is possible to store several slices of confocal data for subsequent point-wise or volumetric filtering operations, increasing robustness and rejecting noise associated with peak detection (i.e. sorting) methods. Memory savings can result, for instance, by providing confocal data from regions of interest which may be a small fraction of the total image. For example, a ball grid array measurement system may use confocal imaging for localized peak detection over a region of 16 pixels× 16 pixels.

Figure 13:
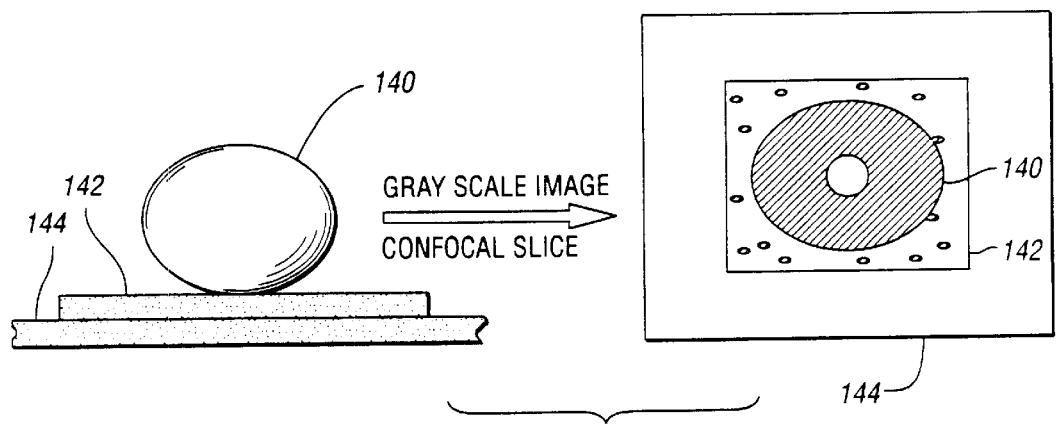
FIG. 13 is a schematic side view, partially broken away, of a spherical mirror (i.e. solder ball) formed on a solder pad and its corresponding confocal slice as viewed from the top of the mirror.

As illustrated in FIGS. 3, 4a, 4b, and 10, in a preferred embodiment where the numerical aperture (N.A.) of the triangulation and confocal subsystems are substantially matched, a single source of illumination is projected and scanned, preferably with a single high speed, solid state deflector, onto the object 120, which may be a solder ball 140 formed on a solder pad 142 which, in turn, is formed on a polished semiconductor wafer 144 as illustrated in FIG. 13. The resulting reflected light is then sampled by the detector system at the separate detectors 118 synchronously. Often, the incident beam will be substantially normal to the object's surface as illustrated in FIGS. 9 and 10.

Alternatively, separate imaging units may be used with sequential data acquisition and the data registered via software within the processor 121 with the disadvantage of extra processing time and additional calibration to compensate for temporal or spatial misregistration. This additional embodiment is not necessarily preferred, but may be acceptable if the system figure of merit is improved. In any case, a solid state deflector has an advantage of random access and high speed windowing and is recognized herein to be advantageous for the high speed confocal-based focusing system described herein.

Certain advantages may be achieved with the use of acousto-optic deflectors, particularly if the access time is fast, corresponding to tens of microseconds maximum. Alternatively, the use of electro-optic deflection technology, preferably in the form of a sequence of electrically activated gratings embedded in a thin film structure, offers potentially exceptional performance, with access times of a few nanoseconds and resolution of several hundred spots. The low delay of these deflectors will provide substantial improvements for inspection of objects in a predetermined or regular arrangement. An example of such a deflector is described in U.S. Pat. No. 4,902,088 (assigned to APA Optics). Micromirror technology may also be employed, provided that access times are fast enough to meet inspection requirements.

Alternatively, acousto-optic deflectors can be advantageous in certain applications with an appropriate compromise between resolution (time-bandwidth product), acoustic velocity (delay), and scan angle. Line rates well beyond video are achievable. For example, $TeO_2$ (Tellurium Dioxide) deflectors operated in longitudinal mode may provide access time on the order of 1 microsecond or less, with 32 or more spots (resolution). The line rates achievable with such a device are extraordinary when applied to localized region-of-interest data acquisition. In certain line scan systems, the limit could become the motion of the translation mechanism used for the part or imaging unit. In some cases, two-dimensional deflection may be preferred to avoid bottlenecks, perhaps with a second acousto-optic device or low inertia mirror. In some cases, it may be advantageous to provide the fast scanning action with a second deflector and laser source confined to the confocal subsystem.

It is instructive to illustrate one of the many novel exemplary operational modes of the multisensor system 110 of the present invention. As illustrated in FIG. 11, a mirrored semiconductor die 202 with "spherical" mirror balls 200 mounted thereon, is scanned. In a first pass, for example, the triangulation-based system will acquire data from the wafer 202 and the balls 200 which partially represents the surface profile. The data is sufficient to rapidly identify defective regions, including missing or defective bumps (i.e. at 42 and 44, respectively, in FIG. 4a), or certain surface defects. For surfaces with diffuse reflection (as illustrated at 40 in FIG. 4a), the triangulation data may be sufficient for height and diameter measurement.

As shown in FIG. 3, the displacement of points corresponding to specular reflection on a perfect mirrored spherical surface measurable with triangulation from the peak of the ball 29 corresponds to only about a 1 $\mu$m height offset for a typical ball with 150 $\mu$m diameter with a triangulation angle 2A of 30°. If, for example, the initial height of the scanning device is chosen such that the surface intersects with the waist of the illumination beam, there is a possibility of rapid merging of the data for peak height and diameter measurement.

Figure 4A:
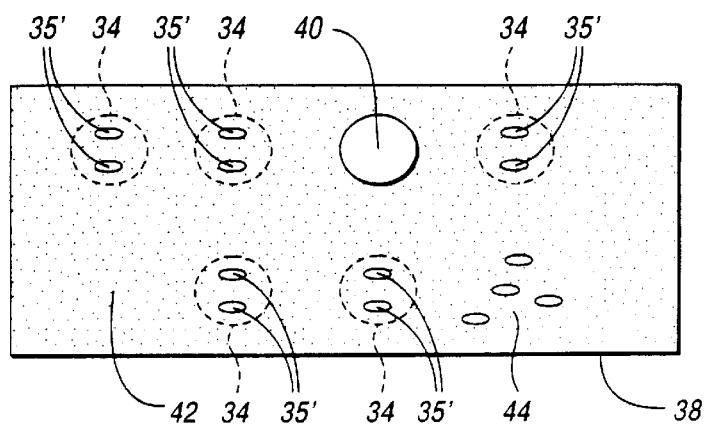
FIG. 4a is a top schematic triangulation-based image of a number of solder balls on a shiny "dummy" wafer utilizing triangulation for obtaining Z measurement, bump presence information and defect information.
Figure 4B:
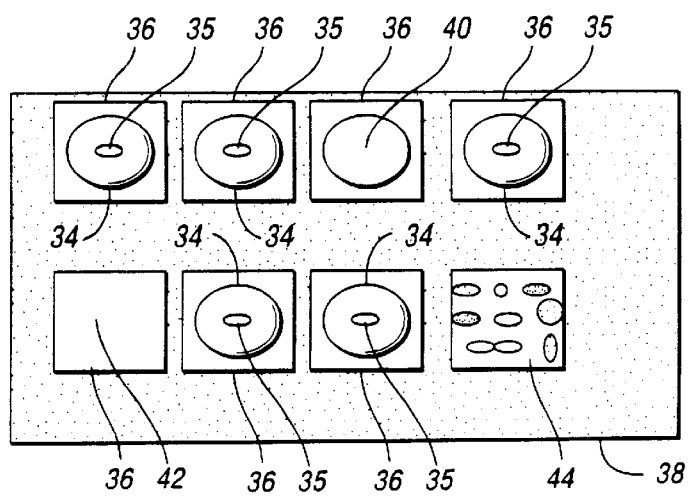
FIG. 4b is a top schematic confocal slice image, similar to FIG. 4a, utilizing a confocal channel to obtain diameter information, Z measurement and defect information.
Figure 5:
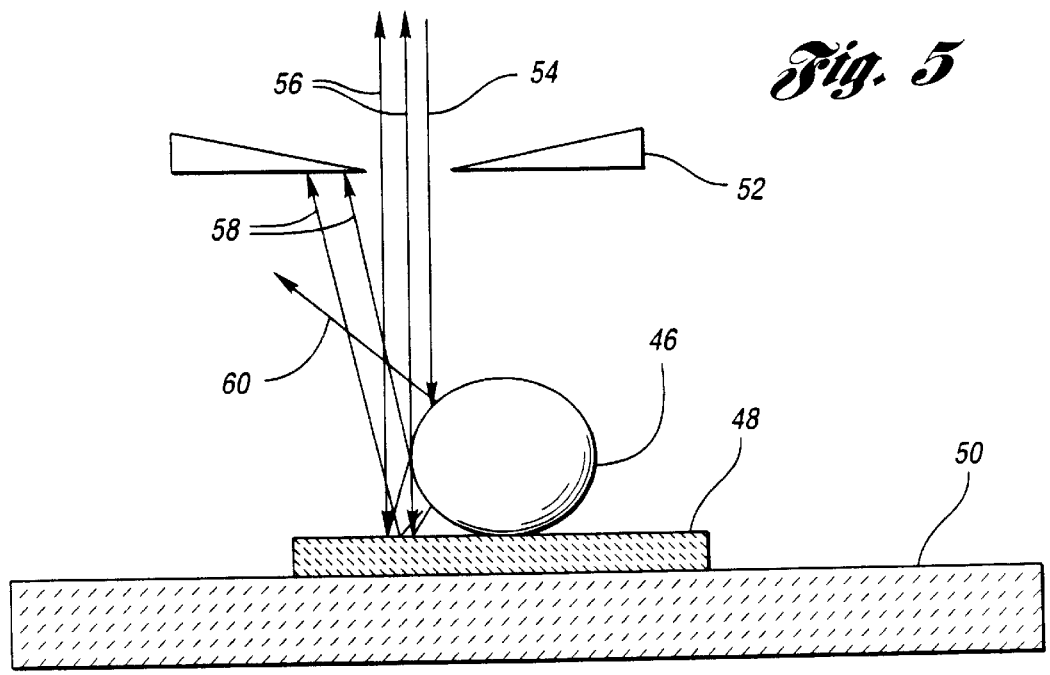
FIG. 5 is a side schematic view of a solder ball on a pad mounted on a substrate and illustrating the filtering action of a spatial filter such as a confocal slit.

Referring to FIG. 4b, simultaneously, data acquired along the confocal channel, can be used to obtain a high contrast image of a ball 34, from which the diameter is estimated. This estimation is superior to that of the triangulation system and camera-based systems; the data is devoid of background noise due to the arrangement illustrated in schematic form in FIG. 5. Often the ball 34 will be specular providing large signals for the confocal channel at the peak location. Furthermore, the high contrast image can be used to locate surface defects which may not be visible in the triangulation data because of occlusion or low signals limited by the diffuse reflection coefficient.

If, for instance, the imaging system 112 is positioned so that the beam waist is at the approximate 50% height level of the ball (nominally), edge definition is maximized, and the contrast will remain high. This favorable condition occurs because of the extreme range of object directional reflectance, spanning several decades. The wafer "mirror-like" return, although reduced well below a maximum, provides for good contrast. The simplified sketch of FIGS. 4b and 13 shows the type of image which is expected from a "spherical mirror" on a flat specular background using a single slice from the confocal channel, near best focus.

As previously mentioned, FIG. 1 shows a solder ball 20 formed on a solder pad 24. A tip 22 of the ball 20 necks down. Specific tradeoffs between depth of focus, object height and background reflectance will influence the contrast.

Figure 6:
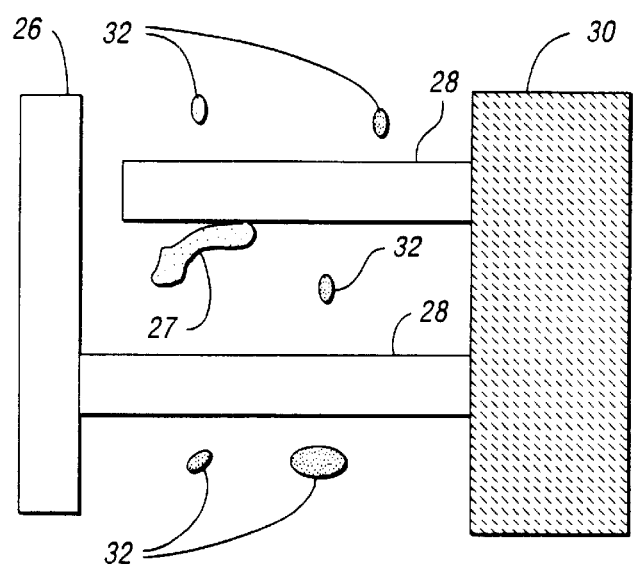
FIG. 6 is a top schematic view similar to that of FIG. 2 after spatial filtering with best focus near the nominal lead and burr locations using the confocal channel.

Similarly, FIGS. 2 and 6 show the resulting images from a single pass with leads near best focus. Likewise, defects on a wafer which correspond to defects in traces, extra material and missing material can be detected.

Figure 7:
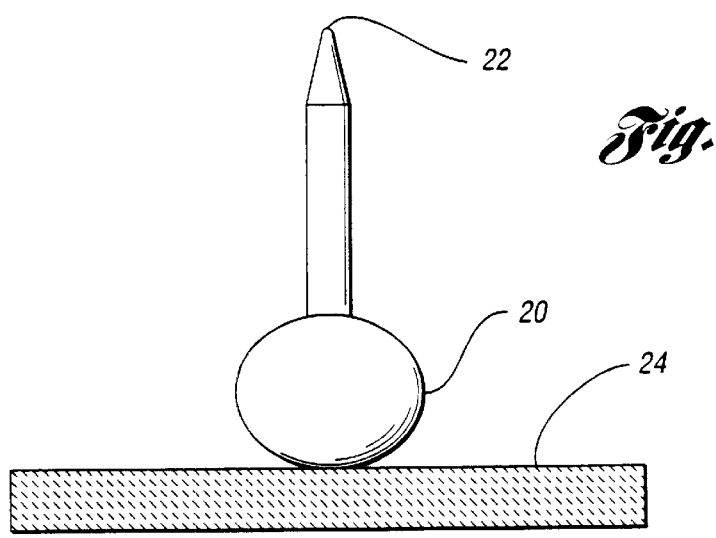
FIG. 7 is a side view of a ball bump on a pad illuminated from the top by laser light and illustrating side lobes outside the point of interest.
Figure 16A:
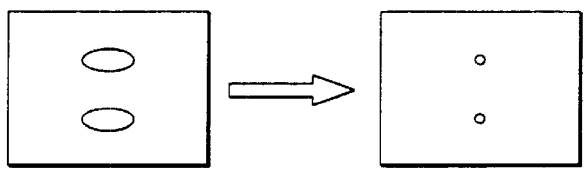
FIG. 16a is a top view of an image of a solder ball obtained through triangulation and processed to obtain peak information to avoid crosstalk.

It has been determined that the standard deviation and absolute accuracy of triangulation-based height measurements is larger than desirable on curved, specular surfaces because of optical crosstalk inherent in triangulation systems necessarily having limited data, as illustrated in FIGS. 3, 7 and 16a. Optical crosstalk will be manifested in the triangulation channel by a localized "contrast reversal" (FIGS. 3, 7 and 16a). In the regions near the peaks shown in FIG. 16a, higher portions of the solder ball will appear lower and vice versa. Hence, the peak detection shown in FIG. 16a is important to the triangulation measurement on such surfaces.

Accuracy can be enhanced and further verification of the correct geometry can be done using the triangulation-based height estimate (the position sensitive measurement corresponding to FIG. 16a), diameter estimate (i.e. FIG. 16b), and lateral location of the intensity maximum to specify the subsequent confocal slices, perhaps in conjunction with high speed "windowing" or region of interest scanning for substantial improvements in speed. These slices may be obtained, for example, with rapid translation of optical elements in the scanner over a narrow range, allowing for high speed.

Figure 14:
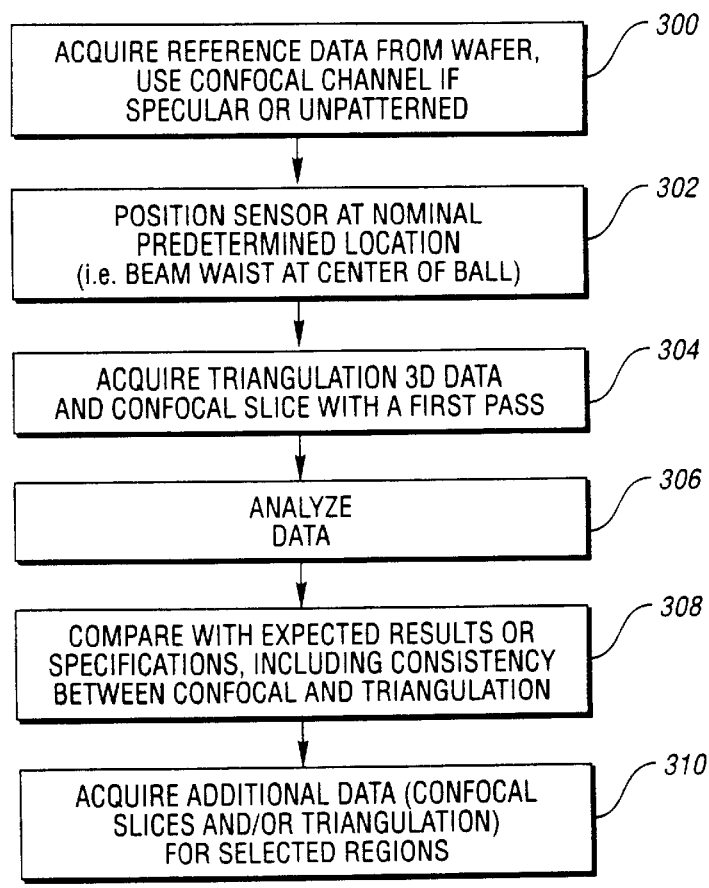
FIG. 14 is a block diagram flow chart illustrating an exemplary method for measuring microscopic targets.

Referring now to FIG. 14, there is illustrated in block diagram, flow chart form an exemplary data collection and processing method of the present invention.

Figure 15:
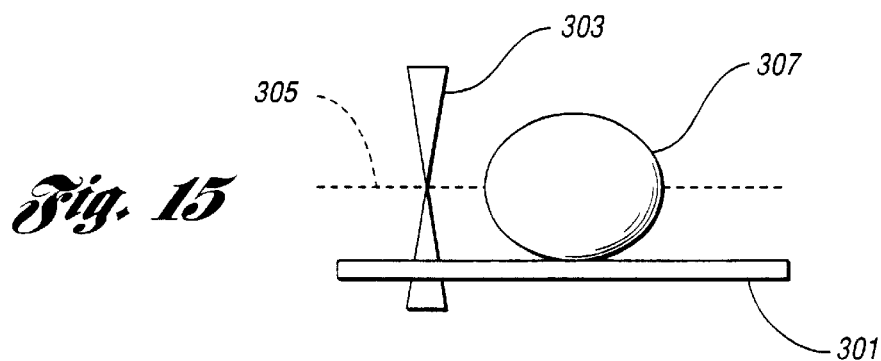
FIG. 15 is a side schematic view of a solder ball on a wafer with a waist of a laser beam at the approximate midway point of the ball.

At block 300, reference data is acquired from a wafer 301 of FIG. 15 or a wafer 38 of FIGS. 4a and 4b. Typically, the confocal channel is used to generate this data if the wafer 301 or 38 is specular or unpatterned.

At block 302, the sensor is positioned at a nominal predetermined location, for example, so that the waist of a laser beam 303 is at the nominal expected center 305 of a solder ball 307 which is a spherical mirror.

At block 304, triangulation 3D data is acquired as well as a confocal slice in a first pass. Such image data is illustrated in FIGS. 4a and 4b for triangulation data and confocal data, respectively, for both specular spheres and for cylinders having diffuse reflection.

Figure 16B:
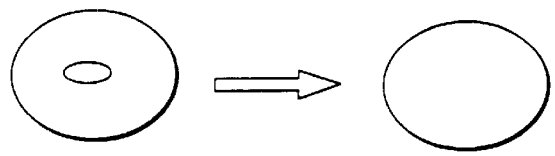
FIG. 16b is a top view of an image of the solder ball obtained through the confocal channel and processed to obtain diameter (i.e. edge) information.

At block 306, the data is analyzed with the processor 121. For a specular object, the 3D triangulation height data is analyzed by isolating the peak information to avoid crosstalk, as illustrated in FIG. 16a. A height estimate is obtained. The confocal diameter and peak position is obtained by analyzing the data from the confocal slice as illustrated in FIG. 16b.

Figure 17:
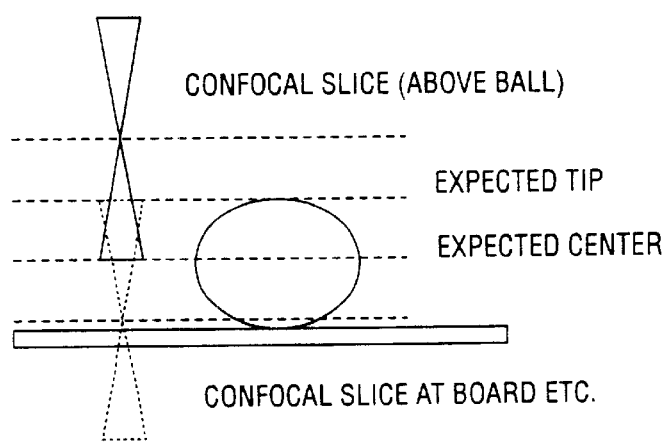
FIG. 17 is a side view of a solder ball on a board illustrating expected tip and center locations as well as confocal slice locations.

At block 308, both the height estimate and the diameter are compared with expected results and/or specifications including expected consistency between confocal and triangulation data as illustrated in FIG. 17 as well as sphericity (i.e. expected conformation to a sphere).

At block 310, additional data, such as confocal slices and/or triangulation data, is acquired for selected regions of interest of the object as also illustrated in FIG. 17.

It is instructive to compare and contrast conventional confocal microscopy with the preferred method utilized herein. Conventional methods use a narrow slit or pinhole, low f/# (high numerical aperture) optics, and small increments for z axis positioning of the object or sensor. Although these principles can be advantageous in carrying out the invention described herein, the requirements for measurement of many microscopic objects can be met with fewer slices at coarse increments. For example, when the system is utilized to measure the depth of reflective objects including solder balls, wafers, traces, conductive epoxy and copper, measured intensity changes continuously with depth, but the optical medium is homogeneous (i.e., air).

The data processing algorithms of the present invention may be implemented in special purpose hardware or in software within the processor 121 and can be applied to either "featureless" surfaces (i.e., a mirror) or rough objects. The slices may be acquired by translating the part or imaging head (conventional) or, alternatively, a plurality of detectors could be used each with a diaphragm (slit or pinhole) as shown in the above-noted USSR patent document and U.S. Pat. No. 5,448,359.

Figure 18:
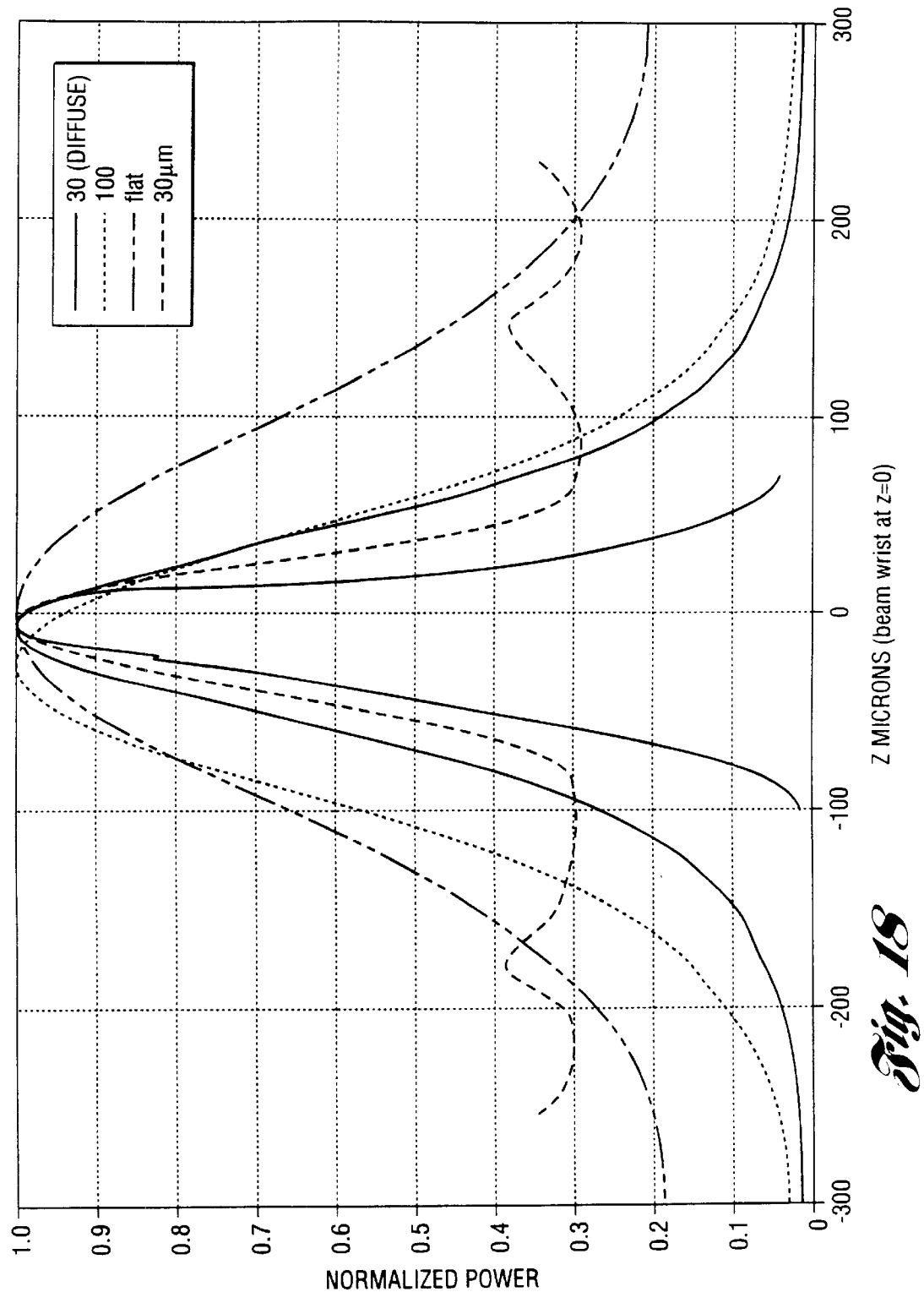
FIG. 18 are graphs of normalized detector power versus height (i.e. beam waist at Z=0) with Gaussian propagation off spherical and flat mirrors with the innermost solid-line graph being of a diffuse surface and wherein the graphs are not necessarily symmetric about the origin and may have varying shapes resulting from the different physical properties of the surface.

Experimental confocal data and simulations indicate that the variation in sensitivity (change in intensity per unit change in depth) is strongly dependent upon the object structure and reflectance characteristics. Profiles of curved specular objects having different radii, plane mirrors, diffuse opaque surfaces, and translucent objects show significant variation. The peak intensity, half width, and asymmetry are variable (see FIG. 18). The curved specular surfaces have focusing power dependent upon the curvature, and produce measurable changes in intensity for relatively small lateral displacements of the spot position on the surface.

The beam propagation characteristics, directional sensitivity, and increased intensity noise produce adverse conditions for measurement. This is in contrast to imaging a diffuse reflector which is "well behaved". The typical assumption of a least squares quadratic fit as taught in the prior art may often be oversimplified, and inadequate for a description of all types of signatures (profiles representing intensity changes with depth). As a result, generalized curve fitting or prediction methods may include "weights" or other adjustments based upon information about the surface.

Curve fitting and peak estimation methods based upon prior information are preferred to estimate the peak location for improved noise immunity. A preferred method of data processing utilizes non-linear and linear filtering for spike removal and smoothing, respectively. This approach, known from the art of image processing, tends to maximize the fidelity of the profile without excessive smoothing. Such a linear filtering algorithm may be implemented with a linear convolution kernel, but preferably will be an adaptive smoothing method. Such algorithms are now commonplace in data processing packages like MathCad 6.0.

Yet another alternative for data acquisition is to use a combination of a predetermined range of translation with a known spacing of a plurality of sensors. The number of detectors and their spacing along the optical axis can be traded off with mechanical height adjustment for a specific measurement speed requirement. For example, a piezoelectric actuator could be used to provide rapid translation over a narrow axial range, or the relationship of optical elements in the transmitter system, including the slit(s) or pinhole(s) changed so as to vary the effective optical path length.

Those versed in the art of confocal imaging will recognize that tradeoffs between measurement speed, optical power, accuracy, cost, and sensor compactness can be analyzed to select an appropriate balance between a plurality of detectors and axial motion with position feedback. Because objects to be imaged with this invention typically produce wide dynamic range requirements, the preference is to maintain high optical efficiency with losses, which result from beam-splitting, minimized. For example, the peak of a solder ball can then be isolated and measured as previously described.

The method and system of the present invention preferably includes a confocal arrangement, but does not exclude the addition of an additional detector in the optically collinear path, which receives collinear light to produce an intensity image without an associated spatial filter. This second detector, which is not spatially filtered, may be used for gray scale measurements and for comparison of the relative intensity of attenuated light with the maximum return from the object 120. This information could be useful for gray scale based measurements, guiding the search process or normalizing the confocal image relative to an intensity maximum if curve fitting is done. This coaxial energy could be collected in any number of ways.

In another mode of operation, absolute height measurements of one of the solder balls 200 of FIG. 11, relative to the bare or patterned die 202 of the wafer 204 can be done using focusing methods taught in the art. When properly fixtured, the dies 202 do not exhibit much warpage. Measuring the die 202 at a few locations (i.e. as indicated by the "X"s in the four corner locations of FIG. 11) using planar surface prediction should be adequate. The four corner locations can be measured using such local fiducials if available, or the bare wafer surface can be measured using the confocal channel. Once again, the imaging head may be positioned along the Z axis to find the general location, and the integrated optical system translated rapidly.

If the scanner 112 includes an acousto-optic deflector or other solid state deflector, for example, an acquisition speed for a region can be minimized by limiting the scan FOV and, for instance, restricting the scan to the X axis only (no Y axis motion for focus measurements mode), quickly moving the Z axis, and recording the intensity. Alternatively, a "ramp" can be generated if the wafer 202 is assumed to be flat over a FOV. In either case, the Z axis location should be recorded as a function of time for best measurement capability.

Fully utilizing the high speed scanner windowing capability available with a beam deflector (say 64 pixels), and the use of a plurality of points for fitting the defocus function would improve reliability while maximizing speed. Speed is the limiting factor for most measurement systems and the method described here would minimize impact for measurement of "featureless" surfaces.

The axial motion may be divided into large range for coarse location of objects, and high speed narrow range operation for measurement. In the former case, the imaging head or part is translated. In the latter case, optical elements or groups may be translated using any of the methods known in the art provided that the proper relationships between the scene, objective lens, and confocal spatial filter are maintained. For example, inspection of microelectronic assemblies might require about 0.25" for coarse location, but an active measurement range of only 0.004" for a low f/# (high numerical aperture) transmitter beam, for instance in the range of f/2 to f/6. The latter motion could be induced with, for example, a piezoelectric translation stage or similar actuator. Fast motion could mandate an increase in the required deflection speed of the scanner 112, leading to an overall advancement for confocal imaging in general. If a deflector with nanosecond response time is available, then the speed will be limited by the axial motion mechanism.

Similarly, of great advantage would be a subsystem to translate the focus position along the optical axis which does not utilize moving parts, or at least only requires miniature, high speed dynamic assemblies. Acousto-optic deflectors, for instance, can change their effective focal length in the scan direction by applying a non-linear, variable frequency waveform. This electrical/acoustical effect is known as the cylindrical lens effect. The device also introduces deflection which, for instance, could be compensated with a high speed, small amplitude deflector, perhaps a micro-mirror. Future advancements in the micro-mechanical technology and integrated optics may lead to development of high speed focus translation methodologies.

Figure 8:
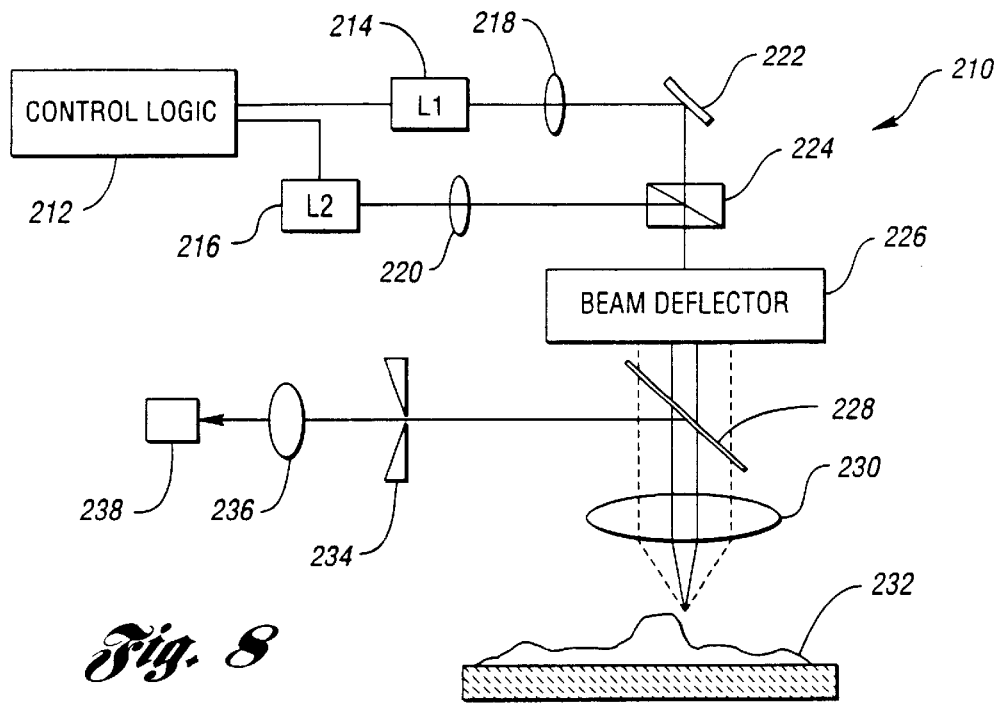
FIG. 8 is a schematic view of a confocal subsystem constructed in accordance with the present invention including control logic to control low and high N.A. laser beams.

Many additional modes of operation can be derived and will be understood by those skilled in the art. For instance, it may sometimes be desirable for the N.A. of the triangulation subsystem be relatively low, providing for good edge contrast over a large depth of field. On the other hand, the highest confocal resolution may be desired. The issue can be addressed by using time, spatial, or wavelength multiplexing and a pair of collinear beams of different wavelength or diameter (f/h). As illustrated in FIG. 8, such a pair of beams introduces dual lateral resolution operation for both confocal and triangulation subsystems.

As illustrated in FIG. 8, a confocal subsystem of an integrated triangulation confocal system is generally indicated at 210. The system 210 includes control logic 212 which controls, by multiplexing, a pair of laser sources 214 and 216. Expanders 218 and 220 expand the laser beams emitted by the laser sources 214 and 216, respectively. A mirror 222 reflects the expanded beams from the expander 218 to obtain a central ray which is combined at beam combiner 224 with the expanded beam from the expander 220.

The system 210 also includes a beam deflector 226 which deflects the combined low N.A. beam and the high N.A. beam to a beam splitter 228, a lens 230 and to an object 230. The resulting beams reflected from the object 230 then are passed through the lens 230, reflected by the beam splitter 228, spatially filtered by a single or multiple slit 234, focused by a lens 236 and detected by a detector 238. Alternatively, the laser sources 214 and 216 could have different wavelengths.

In yet another embodiment of the present invention, multiple slits with varying dimension could be used to provide variable sensitivity and depth of field. This option requires additional optical elements (including detectors) and can be readily implemented by those skilled in the art.

If a solid state deflector is used, either acousto-optics or electro-optics diffraction gratings, with wavelength multiplexing, then additional optics will be needed to expand the scan width according to the wavelength ratio. With wavelength multiplexing, spectral filters can be used to provide discrimination and eliminate crosstalk.

Time multiplexing would preferably be implemented with two lasers which are pulsed in sequence. Then, either the confocal or triangulation channels or both are read. The advantage is dual lateral resolution operation for both the confocal and triangulation modes.

Those skilled in the art will recognize the versatility of the invention, and extensions and operational principles which are within the spirit of the invention. The feature of multiple beams or slits in a multiplexed system, either beam being available for use in the triangulation and confocal channels, provides a choice of expanded or narrow depth of field, which can be advantageous for measurement of objects with an extended depth range. For example, the high N.A. channel may be used to locate defects in thin conductive, dielectric layers, or provide contrast improvement for surface inspection, while the wider range is useful for examining interconnects.

This foregoing description shows illustrative embodiments and principle of operation but should not be regarded as restrictive. The versatility of measurement methods and systems is a direct benefit of the invention which is limited only by the following claims.

What is claimed is:

1. A method for developing dimensional information about an object on a specular background utilizing a scanning system having a sensor, the scanning system scanning an illumination beam of electromagnetic energy, the method comprising the steps of:

determining reference data based on an illumination beam reflected from the specular background;

providing the sensor with a first detector capable of obtaining triangulation data and a second detector capable of obtaining confocal data;

positioning the sensor based on the reference data so that a waist of the illumination beam substantially coincides with an expected predetermined 3D location of the object so as to enhance contrast and obtain triangulation sensor data and confocal sensor data; and processing the triangular sensor data and the confocal sensor data to obtain the dimensional information.

2. The method as claimed in claim 1 wherein the object is a bump and wherein the dimensional information includes a height estimate of the bump.

3. The method as claimed in claim 2 wherein the dimensional information includes information as to whether the bump is defective or not.

4. The method as claimed in claim 1 wherein the object has a spherical, mirror-like surface and wherein the object is mounted on a planar mirror-like surface of the background.

5. The method as claimed in claim 4 wherein the dimensional information includes a diameter for the spherical mirror-like surface.

6. The method as claimed in claim 1 wherein the dimensional information includes 3D information.

7. The method as claimed in claim 1 wherein the object is a micromechanical device.

8. The method as claimed in claim 1 wherein the object is a conductive trace.

9. The method as claimed in claim 1 wherein the object is an interconnect on a semiconductor device.

10. The method as claimed in claim 1 wherein the triangulation sensor data and the confocal sensor data are processed with a predetermined measurement algorithm.

11. The method as claimed in claim 1 wherein the triangulation sensor data and the confocal sensor data have substantially perfect temporal and spatial registration before the step of processing.

12. The method of claim 1 wherein the object has a diameter and wherein the dimensional information is a measurement of the diameter.

13. The method of claim 1 wherein the object is a defect of or on a wafer.

14. The method as claimed in claim 1 wherein the dimensional information includes height information.

15. The method as claimed in claim 1 wherein the step of processing the sensor data is performed in combination to produce the dimensional information.

16. The method as claimed in claim 1 wherein the object has a diameter and wherein the dimensional information includes diameter information and wherein the method further comprises the step of locating a region of the object for further data acquisition based on the dimensional information.

\* \* \* \* \*